United States Patent
Goebel

(10) Patent No.: US 7,967,780 B2
(45) Date of Patent: Jun. 28, 2011

(54) GASTRO-ESOPHAGEAL REFLUX CONTROL SYSTEM AND PUMP

(75) Inventor: Fred G. Goebel, Wilhemsfeld (DE)

(73) Assignee: Kimberly-Clark Worldwide, Inc., Neenah, WI (US)

(*) Notice: Subject to any disclaimer, the term of this patent is extended or adjusted under 35 U.S.C. 154(b) by 940 days.

(21) Appl. No.: 11/846,888

(22) Filed: Aug. 29, 2007

(65) Prior Publication Data
US 2009/0062725 A1 Mar. 5, 2009

(51) Int. Cl.
*A61M 29/00* (2006.01)
(52) U.S. Cl. .......... 604/100.01; 604/96.01; 604/101.02; 604/97.01
(58) Field of Classification Search .......... 604/28, 604/31, 96.01, 100.01, 101.05, 101.01, 103.03, 604/103.06–103.08, 131
See application file for complete search history.

(56) References Cited

U.S. PATENT DOCUMENTS

| | | | |
|---|---|---|---|
| 4,529,397 A | 7/1985 | Hennemuth et al. | |
| 5,135,467 A | 8/1992 | Citron | |
| 5,379,773 A * | 1/1995 | Hornsby | 600/466 |
| 5,718,685 A * | 2/1998 | Roewer et al. | 604/100.01 |
| 6,050,932 A | 4/2000 | Franchi | |
| 6,551,272 B2 | 4/2003 | Göbel | |
| 7,229,402 B2 | 6/2007 | Diaz et al. | |
| 2008/0154191 A1 | 6/2008 | Göbel | |
| 2008/0167607 A1* | 7/2008 | Pfeiffer et al. | 604/97.01 |

FOREIGN PATENT DOCUMENTS
DE 20 2006 002 832 U1 7/2007

OTHER PUBLICATIONS

M. Orozco-Levi, M. Félez; E. Martinez-Miralles; J.F. Solsona; M.L. Blanco; J.M. Broquetas; A. Torres, Gastro-Oesophageal Reflux in Mechanically Ventilated Patients: Effects of an Oesophageal Balloon, ERS Journals Ltd 2003, European Respiratory Journal, pp. 348 to 353.
Written Opinion of the International Searching Authority / International Search Report, dated Jan. 12, 2009.

* cited by examiner

*Primary Examiner* — Kevin C Sirmons
*Assistant Examiner* — Bradley G Thomas, Jr
(74) *Attorney, Agent, or Firm* — Dority & Manning, P.A.

(57) ABSTRACT

An enteral feeding unit that reduces the occurrence of gastro-esophogeal-pharynegal reflux during feeding includes an automatable feeding pump with a feedback sensor for sensing a relative pressure in a patient's stomach and esophagus, and a regulator system for controlling and monitoring feeding rate to the patient as a function of the relative gastro-esophageal pressure. The system includes a stomach probe that provides a fluid-tight closure of the esophagus. The stomach probe includes a tampon-bladder for watertight closure of the esophagus, in which the tampon-bladder is formed of flexible and/or elastic material. At least an inner cavity of the bladder is provided for the reception of a fluid medium. A prescribed pressure for the medium in the tampon-bladder (53) is maintained by an inner lumen forming the stomach probe, from which an outer hose-like lumen (62) extending to the tampon-bladder (53) is so arranged that between the outer lumen (62) and the inner lumen (61) a channel is formed connected to the inner cavity of the tampon-bladder (53) arranged on the outer lumen (62) by a number of openings (57). The inner cavity (58) of the tampon-bladder (53) is connected via a canal formed between the inner and outer lumina (62) with a suitably graded reservoir or equalizing vessel for the liquid medium situated above the tampon-bladder and outside the patient.

18 Claims, 4 Drawing Sheets

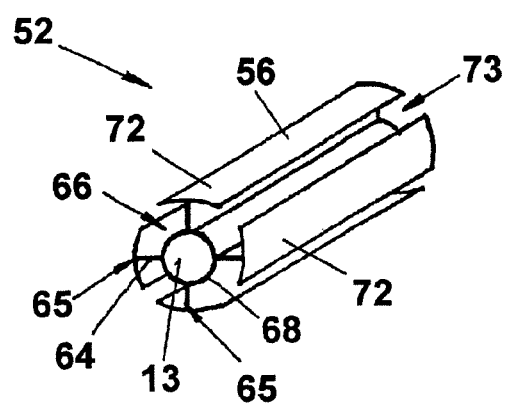
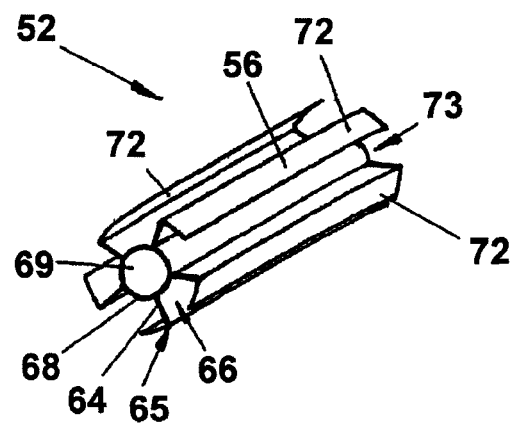
Fig. 6
Fig. 7
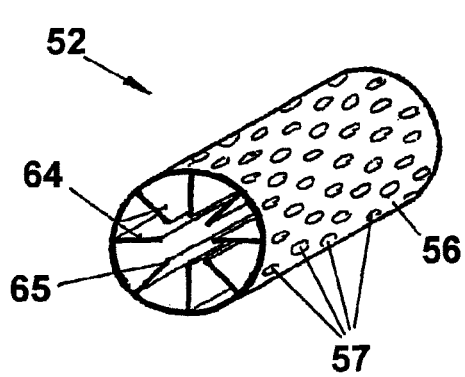
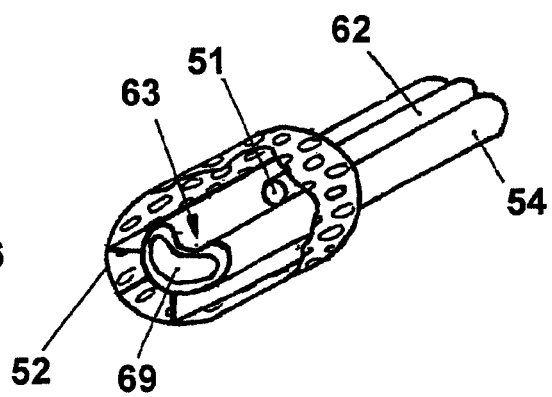
Fig. 4
Fig. 5

GASTRO-ESOPHAGEAL REFLUX CONTROL SYSTEM AND PUMP

FIELD OF INVENTION

The present invention relates to a system for preventing gastro-esophageal reflux by regulating or counterbalancing stomach pressure generated during and in between episodes of gastric-enteral feeding of a patient.

BACKGROUND

Spontaneous release of gastric pressure is often associated with reflux, which is the transport of stomach contents to the pharynx. Gastro-esophageal "reflux fluid" as used herein includes any gas, any liquid, any partially solid and liquid substance or any material that can be expelled from the stomach into the patient's pharynx. Fluids that commonly accumulate in the stomach of a tube-fed patient include the tube-feeding formula, swallowed saliva (more than about 0.8 L/day), gastric secretion (about 1.5 L/day), and regurgitated small bowel secretion (about 2.7 to 3.7 L/day) into the stomach. Gastro-esophageal reflux (GER) often appears as an intermittent more or less massive, bolus-like regurgitation of stomach contents, but also can manifest as a continuous, silent ascension and descension of liquid and solid material between the gastrointestinal tract and the pharyngeal tract. GER alongside of gastric feeding and decompression tubes in intubated patients, both ventilated and spontaneously breathing, is a common problem in ICU therapy, being associated with a high infection relevance.

Especially under so called intra-gastric or intra-duodenal feeding, the incidence of reflux of stomach contents into the pharynx of the patient is increased. Gastric, duodenal or enteral feeding is a form of hyper-alimentation and metabolic support in which nutrient formulas or medicaments are delivered directly to the gastrointestinal tract, either the stomach or the duodenum. In the majority of cases, nutrient administration is accomplished through use of a tube based device or system, delivering the nutrient through the patient's pharynx and esophagus directly into the stomach, the duodenum or small intestinum (jejunum), often referred to as so-called enteral feeding. Certain enteral feeding devices include pumps that deliver feeding fluid to the patient. Other enteral feeding devices rely upon gravity to move the feeding fluid from a container (suspended above patient level) to the patient.

Enteral tubes for providing food and medication to a patient have been used in medical settings for many years. Examples of enteral feeding devices are described in U.S. Pat. Nos. 4,666,433; 4,701,163; 4,798,592; and 4,685,901, which are hereby incorporated herein in their entireties for all purposes by this reference. In critical care therapy, gastric (enteral) feeding is usually performed via so called naso-gastric decompression catheters (NG-tubes), which are primarily used to release pressure building up in the stomach of a patient. Excessive gastric pressure may result from the accumulation of liquid intestinal secretions, feeding solution applied into the stomach or duodenum, abdominal motility, body movement or positioning of the patient, or through normal formation of gas. For decompression of gastric pressure and drainage of gastric contents, such patients may be intubated with so called naso-gastric or oro-gastric tubes or probes. An example of one such stomach probe is described in German Utility Model Application No. 202006002832.3. Another is described in U.S. Pat. No. 6,551,272 B2, which is hereby incorporated herein in its entirety for all purposes by this reference.

Because solids and/or higher viscosity liquid secretions frequently obstruct the drainage lumen of a stomach probe, in many cases stomach probes insufficiently decompress the stomach. The insufficient decompression of the stomach permits reflux of fluids through the esophageal lumen alongside the NG tube. Further, instead of preventing GER, the literature describes the trans-esophageal passage of the rigid decompression tube shaft as itself impairing the seal efficacy of the esophagus and its sphincters by partially opening the sphincters and thus facilitating the ascension of secretions from the stomach into the pharynx alongside the tube shaft. Studies have shown that while GER occurs in about 15% of supine positioned patients without NG tubes, the prevalence of GER in supine positioned patients with NG tubes may increase to about 80% of cases.

Moreover, GER occurs in critically ill patients even in the absence of nasogastric (NG) tubes and enteral delivery of feeding solutions. Up to 30% of patients who are kept in the supine position are estimated to have GER.

The free communication of secretions between pharynx and stomach often results in a state of continuous ascension and decension of high volumes of colonized fluids, which may be on the order of several hundred milliliters per day or even on the order of liters per day. Typically, after about 4 to 6 days of mechanical ventilation, a mixed bacterial flora becomes established and populates the upper GI-tract as well as the entity of the pharyngeal, i.e., cranio-facial cavities. Such colonized material may pool in predisposed spaces such as the maxillary or sphenoidal sinuses, representing a most relevant source for bacteria inducing so called ventilator-associated pneumonia (VAP) as well as an origin for the septic spread of bacterial pathogens.

The free communication between the pharyngeal and gastro-intestinal compartment also impairs gastric delivery of enteral feeding solutions, which frequently becomes a problem in administering sufficient calories in the natural way via the upper GI-tract, and may require expensive and complication associated par-enteral feeding. In many cases, one can observe that feeding solution runs out of the patient's oral and nasal openings, implying that the reflux volume has been high and that all cranio-facial surfaces have been covered with a layer of bacteria feeding nutrients, supporting a major reservoir of pathogenic bacteria, especially in the etiology of VAP.

Preventive strategies against reflux of gastro-esophageal contents were essentially medicinal/antibiotic based, as for example so-called selective digestive decontamination (SDD) of the pharynx and the stomach by application of topical, non-resorbable antibiotics. Additionally, oral care procedures are being performed on most ICU wards, whereby the oro-pharyngeal cavity is cleaned by a swab or a brush, applying a small volume of water or cleaning solution into the oro-pharynx. Further, medication has been administered to long term ventilated patients, preventing bacterial colonization of the stomach by keeping the stomach pH within an acidic, antiseptic range.

Perhaps the most frequently practiced and probably most efficient preventive measure against reflux of gastro-esophageal contents has been to elevate the patient's upper body into a semi-recumbent position, thereby reducing the ascension of colonized gastric material into the pharynx. At least two studies have shown a reduction of GER when critically ill patients are kept in the semi-recumbent position. Thus, patients undergoing mechanical ventilation are usually put in a supine or a semi-recumbent body position.

When gastrointestinal motility is normal, secretions and ingested fluids are propelled forward by the upper gastrointestinal tract with little difficulty. Significant gastrointestinal dysmotility, ranging from moderate delay in gastric emptying to marked gastric paresis, has been described in patients with a variety of clinical conditions such as burns, sepsis, trauma, surgery, and shock. GER frequently can be observed during tracheal intubation and mechanical ventilation, where sphincter function and gastric motility may be impaired as a side effect of the analog-sedating medication applied, and an extended period of demobilization of the patient in supine position. In order to prevent reflux under gastric feeding, respectively to support gastric and duodenal motility and emptying, ICU clinicians administer special drugs like e.g. metoclopramid.

When the combination of feeding solution blended with gastro-intestinal fluid can freely communicate between the upper GI tract and the entity comprised of all the cranio-facial spaces connected to the patient's pharynx, the patient can suffer severe consequences in several regards:

First, feeding solution is lost, and necessary calories cannot be administered successfully, resulting in the need for costly prolonged par-enteral patient feeding.

Second, the mucosal surfaces of the cranio-facial cavities are getting covered intermittently with nutrients contained in the feeding solution, providing ideal growth conditions for bacteria, increasing the risk of colonization with bacteria relevant for the development ventilator associated pneumonia (VAP). Pharyngeal secretions, descending via the tracheal tube cuff to the distal airways are known to be a major cause of pulmonary infections in the intubated and ventilated patient.

Third, feeding solution, which is pooling in the remote cranio-facial cavities as the naso-pharynx and the paranasal sinuses, cannot be removed by state of the art care techniques, may turn into a purulent state and become a permanent source for VAP pathogens or bacteria causing septic complications, by so called translocation of the bacteria through the inflamed mucosa from the purulent pool into the blood stream.

The measurement of esophageal and gastric pressures with balloon-tipped catheters has been employed with great success over the past half century to delineate the physiology of the respiratory system. The determination of so called transdiaphragmatic pressure, which is usually detected by sensing the pressure gradient between a balloon element disposed in the esophagus and a balloon element disposed in the stomach or intestine, has led to the development of according measuring probes and pressure sensing hardware, whereby the balloons are small in dimension and incapable of effecting an esophageal seal function. The related hardware is set for pressure detection exclusively and cannot actively regulate a seal pressure gradient.

In recent years there have been clinical attempts to effect an esophageal balloon seal against gastric material ascending from the stomach into the pharynx, using probe material designed for esophageal bleeding intervention (Sengstaken Blakemore tubes). Orozco et al. (details) were able to show a significant reduction of gastro-esophageal reflux. However, the structures of the esophageal wall react extremely sensitively to persistent pressure or organ wall distension. Thus, such conventional blocking techniques, in which the hull of a sealing bladder structure is placed under tension, are not, or only with limitations, desirable in the case of the esophagus. Due to the potential esophageal trauma risk, the application period of the stationary pressured balloon was limited to 8 hours.

A stomach probe such as described in German Utility Model Application No. 202006002832.3 has an esophageal bladder and enteral feeding tube that are integrated such that the feeding tube sits at or near the center of the bladder when used in a patient. The feeding tube has a thin-walled bladder associated with the feeding lumen. Around the feeding lumen is either one or a plurality of ferrules that are used to conduct air or other gas along the length of the bladder. A stomach probe of this type has a lumen that is located on the delivery cannula in the region of the inflatable bladder, which arrangement guarantees a rapid equalization of volume between sections or partial volumes of the inflatable bladder. The lumen is arranged so that a channel is formed between the lumen and the delivery cannula, which is connected to the interior of the inflatable bladder via a number of openings, and which is arranged on the lumen. The interior of the inflatable bladder is connected to means for producing pressure in the inflatable bladder via the channel formed between the delivery cannula and the lumen. The lumen is thereby kept open by stent-like devices or spacers between an outer and an inner wall of the probe or the delivery cannula of the stomach probe. However, a stomach probe of this type is therefore much more complicated to produce than conventional stomach probes without a lumen, for example.

SUMMARY OF THE INVENTION

According to the present disclosure, a pressure gradient based esophageal seal is provided that is optionally self-adjusting to continuously changing seal pressure requirements as well as to long-term organ compatible and atraumatic intra-esophageal bladder placement.

The present disclosure rectifies the disadvantages associated with conventional gastric or duodenal decompression and feeding catheters. The present disclosure includes a decompression or feeding probe that enables a clinician to close off or seal a patient's esophagus over extended periods well in excess of eight consecutive hours, without causing patient irritation and without causing deleterious effects on the esophageal structures. By interrupting the free communication between the gastro-intestinal tract and the upper respiratory tract, gastro esophageal reflux of stomach contents into the pharynx can be reduced. Thus, the efficacy of gastro-duodenal application of feeding solution can be improved, and the amount of bacterial colonization of the pharynx and the adjunct cranio-facial cavities can be lowered.

In one aspect of the disclosure, a pressure sensor element placed inside the stomach continuously senses intra-gastric pressure and reports to a control device/unit that accordingly regulates the filling pressure of an esophageal placed organ sealing bladder. In one mode, the control device/unit regulates the filling pressure of the esophageal placed organ sealing bladder according to a pressure that is manually set at a predetermined constant pressure. This is the manually set and operated stationary mode. In another mode, the control device/unit regulates the filling pressure of the esophageal placed organ sealing bladder according to a pressure that is constantly changing and that is the pressure measured by a second pressure sensor placed in the esophagus. This is the self-regulated or dynamical mode. Each mode enables the setting of a user determined continuous seal pressure gradient by which the pressure in the esophageal seal bladder exceeds the intra-gastric pressure, thereby effecting a pressure gradient that serves a reflux-preventive esophageal seal function against gastro-intestinal contents ascending from the stomach past the esophageal seal bladder.

The control device/unit can be connected or integrated into a feeding pump that delivers the feeding solution to the patient. Such integration enables the above described regulation of a pressure gradient-based esophageal seal function, preventing especially the ascension and loss of pharyngeal feeding fluid into the pharynx, as well as creating a pressure gradient between the stomach and the duodenum, facilitating the spontaneous emptying of the stomach and intestinal directed flow of feeding solution. The combination of seal pressure control device and feeding pump provides the ideal tool for the user not only for improving the efficacy of enteral feeding, but also, reducing the amount of GER in the periods intermittent of gastric feeding, thus having a preventive effect on the development of VAP. Further, the feeding pump unit can integrate special control algorithms that improve the intestinally directed uptake of feeding solution and reduce potential traumatic effects of a permanently exposed seal force on the pressure sensitive esophageal structures.

Additionally, a particular oro/naso-gastric/duodenal catheter design for combined use with the above described control device or control device/pump combination is described. The catheter can be provided with a lumen, which is located between the delivery cannula and an inflatable tampooning esophageal bladder and which is connected to the interior of the inflatable bladder. The catheter can be produced by a relatively simple technique, and at the same time guarantees adequate volume equalization between the partial volumes of the inflatable bladder. The catheter desirably includes: a tube having at least a double lumen, a gastric pressure sensor element and an esophageal tampon bladder, whereby the gastric pressure sensor and the tampooning esophageal bladder are connected to a pressure sensing and regulating control-device. The esophageal bladder can be pre-shaped to a residually dimensioned preformed diameter that includes a plurality of pleats that can intermesh with the mucosal folding of a patient's esophagus. In this way, in order to effect a sufficient seal of an expanding esophageal lumen, the pleated wall of the tampon bladder need not be stretched by increasing the internal pressure, but rather merely unfolds at the same pressure and can therefore resize itself sufficiently to cover the physiologic axially directed folding of the esophageal mucosa at the lowest possible filling pressure. This unfolding mechanism essentially effects a tamponade of the remaining open lumen in the esophagus, instead of creating a pressure intensive organ blockage, as effected by conventional compliant, expandable bladder materials. Further, the tampon carrying segment of the catheter shaft may be equipped with a special shaft profile, enabling the esophageal placed tampon to withstand peristaltic contractions by performing an intra-tampon volume shift of the applied filling medium from the portion distal of the peristaltic contraction into the portion proximal and already released of the peristaltic contraction.

In another aspect, the present invention relates to a method or process for effectively reducing gastric reflux into a patient's esophagus. The method involves: providing an enteral feeding tube having at least a double lumen, an esophageal seal bladder and a gastric pressure sensor element (e.g., gastric balloon); inserting said enteral feeding tube into said patient's upper alimentary canal, to position said gastric balloon in said patient's stomach and said esophageal bladder in said patient's esophagus; receiving from the gastric pressure sensor element an intra-gastric pressure signal that can be averaged using a filter algorithm; setting of a user determined gradient value that is continuously added to the sensed actual gastric pressure, thereby defining a relative level of esophageal pressure that should be applied to seal the esophagus from gastro-pharyngeal reflux, respectively enabling the built-up of a pressure gradient directed from the stomach towards the duodenum, facilitating the emptying of the stomach contents into the distal digestive tract.

Other features and advantages of the present system and individual devices or components will become evident from the following detailed description. It is understood that both the foregoing general description and the following detailed description and examples are merely representative of the invention, and are intended to provide an overview for understanding the invention as claimed.

BRIEF DESCRIPTIONS OF DRAWINGS

FIG. 4 shows a perspective view of a shaped body shown in FIGS. 2 and 3, according to a first embodiment.

FIG. 5 shows a perspective view of a delivery cannula.

FIG. 6 shows a perspective view of a disclosed shaped body according to a second embodiment.

FIG. 7 shows a perspective view of a disclosed shaped body according to a third embodiment.

DETAILED DESCRIPTIONS OF ILLUSTRATIVE EMBODIMENTS OF THE INVENTION

The present invention describes a device and method, which effects a static or dynamical, low irritating, long-term organ compatible and stationary seal function within the esophagus, intending to interrupt the above described free communication of secretions and gastric material between the upper respiratory tract and the gastro-intestinal tract.

Figure 1:
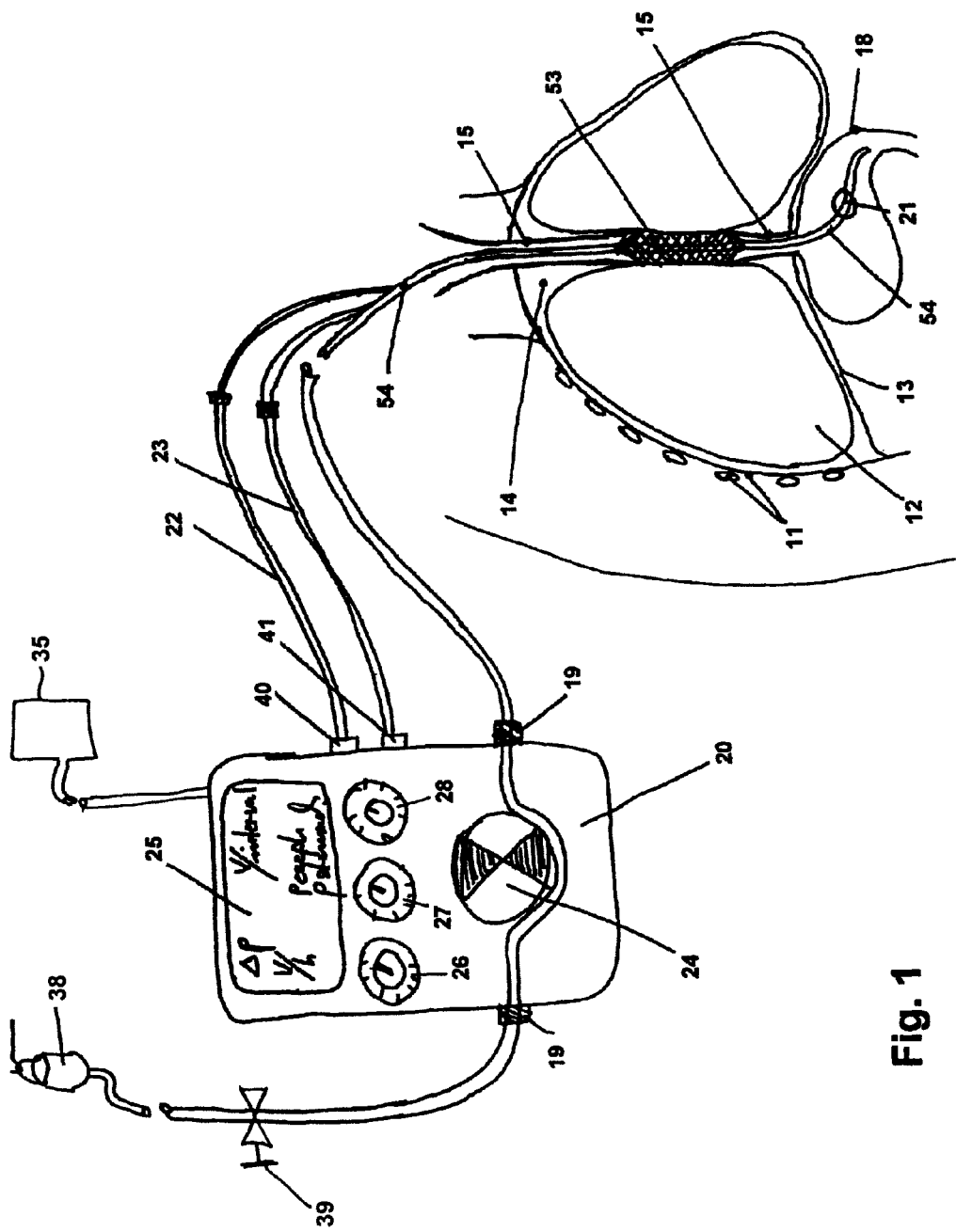
FIG. 1 is a general schematic representation of an embodiment of the present invention as inserted in a silhouette outline of a patient's head, torso and upper abdomen with a diagram of a pump system according to an embodiment of the present invention.

Referring to FIG. 1, which schematically illustrates a cross-section of part of a patient's torso, the patient's chest cavity wall 11, lungs 12, diaphragm 13, intra-thoracic space 14, esophagus 15, and stomach 18 are depicted. Also depicted in FIG. 1 is a presently preferred embodiment of an anti-gastro-esophageal reflux device for use during enteral feeding as it may operate in situ in a patient's thorax in combination with a feeding pump function/unit. As schematically illustrated in FIG. 1, an embodiment of a seal system includes a combination of a gastric tube 54 inserted through the nasal or oral cavity, passing through the esophagus 15, and terminating in the stomach 18. The oro/naso-gastric tube 54 has a pressure sensing balloon 21, which alternatively can be provided by an electronic pressure sensing element 21, situated near the end of the tube's tip that is situated in the stomach 18. This gastric balloon/sensor 21 is connected to a respective filling/communication line 23. Proximal of the gastric sensor balloon 21 is situated an esophageal sealing bladder 53 with a filling line 22 along or integrated in the shaft of the naso-gastric tube 54.

As schematically shown in FIG. 1, in accordance with a presently preferred embodiment of the invention, a decompression/feeding tube 54 can be specially designed for combined use with a sensing and regulating device 20, which is configured to receive signals from one or more pressure sensors and is configured to regulate the seal force in the esophagus 15 according to the sensed pressure(s). As schematically shown in FIG. 1, the control device 20 can be integrated with a feeding pump 24, such as a roller pump 24, or similar mechanism used in gastric feeding pumps for delivering feeding solution from a reservoir 38 via a tube segment 19 to the patient's stomach 18. The combination provides the benefit of a regulated reflux-preventive esophageal seal 53, especially suited for the requirements of enteral feeding of a critically ill patient.

The control device 20, which desirably is configured to receive and process signals from pressure sensor 21 and to regulate the seal force exerted by the bladder 53 on the wall 16 of the esophagus 15, desirably can include mechanical pump/pumps, pressure transducers, analog-digital-converters, and a logical/control unit such as a programmable logic controller and/or a programmable microprocessor.

The control device 20 desirably can be configured to continuously monitor and optionally display the actual intra-gastric pressure sensed by sensor 21 and to regulate the inflation pressure of the esophageal seal bladder 53 so as to ensure a user determined pressure gradient ($\Delta P$) between the sealing esophageal bladder 53 and the pressure inside the stomach 18 to seal against. As schematically shown in FIG. 1, the control device 20 or regulator mechanism can be provided with a display 25 for feedback from sensors and other parameters. The display 25 can be configured to provide a visual display of the user determined pressure gradient between esophageal and gastric pressure ($\Delta P$), the actual and desired volume/unit time (V/h) of nutrient to be fed to the patient, the esophageal pressure ($P_{esophagus}$) sensed by the seal bladder 53, and the gastric pressure ($P_{gastric}$) sensed by the gastric sensor 21.

The control device 20 or regulator mechanism can be provided with manual controls for regulating the rate at which feeding solution is supplied to the patient and other parameters. As schematically shown in FIG. 1, the control device 20 can be provided with a manual input mechanism 26 option that enables the user to set the magnitude of the desired pressure gradient $\Delta P$. As schematically shown in FIG. 1, the control device 20 can be provided with a manual input mechanism 27 for controlling the volume of nutrient to be fed to the patient, a manual input mechanism 28 for controlling the delivery time during which nutrient is to be fed to the patient, and a manual input mechanism 39 for controlling the connection of the system to a feeding container 38 that contains the feeding solution.

By continuously adding the user determined seal pressure gradient ($\Delta P$) to the actual intra-gastric pressure detected by sensor 21, the force exerted by the esophageal seal 53 against the esophageal tissue 16 can be continuously reduced to the required minimum and thus reduce accordingly the likelihood of pressure induced trauma that otherwise might be caused by continuous, inappropriately high seal pressures. If the level of intra-gastric pressure is relatively low, then the esophageal seal force and trans-murally effected force is commensurately relatively low. If the level of gastric pressure increases, then the esophageal seal pressure only is increased by a gradient ($\Delta P$), which can be determined by the user as being sufficient for reflux prevention. Stationary, high seal pressure gradients that exceed the actually required seal force thus can be prevented.

Alternative to a continuous adjustment of esophageal seal pressure to actual intra-gastric pressure, the addition of the user determined seal pressure gradient ($\Delta P$) to the actual intra-gastric pressure can be performed intermittently within time intervals that can be pre-set or fixed by the user in the control device 20 as by a manual input mechanism 28 for controlling the time interval for feeding nutrient to the patient or determined by a manual mode, whereby the user determines the addition of the seal gradient ($\Delta P$) to the gastric pressure by e.g. manually entering the desired seal gradient $\Delta P$, which remains effective till the manual adjustment is repeated.

Integrated into or connected to a feeding pump 24, the control device 20 for regulating the esophageal seal force can be configured to actively keep the seal pressure of the esophageal bladder 53 in dynamic accordance with the actual intra-gastric pressures reached under ongoing and post-gastric feeding, so that a seal-sufficient pressure gradient ($\Delta P$) between intra-esophageal pressure and the intra-gastric stomach pressure can be continuously maintained. The control device 20 can be configured to control the feeding pump unit 24 to further control the relative feeding rate to a patient as a function of the gastric pressure sensed through the gastric pressure sensor 21, thereby preventing critical esophageal seal forces from being reached and feeding the nutrient under optimal pressure conditions and/or during optimal feeding periods.

Algorithmic Control

Analogous to a ventilation control technique, such as described in U.S. Pat. No. 7,040,321 B2, which is incorporated herein in its entirety for all purposes by this reference, the present enteral feeding system also desirably can use an algorithmic control for controlling the feeding pump. A possible example of such an algorithmic control could include the following. After placement of a gastric probe 21 and activation of the system, the control device 20 can be configured to pump a defined volume of filling fluid via filling line 23 into the gastric balloon 21 to fill the balloon, which is preferably smaller than the volume of the gastric balloon 21 in its freely inflated pre-shaped state. As schematically shown in FIG. 1, the control device 20 can be configured to operate a pump 41 connected via filling line 23 to the gastric pressure sensing balloon 21 to fill the balloon 21.

By inflating the gastric sensor balloon 21 partially, it remains in a floppy non-extended state, being able to respond to slightest changes of intra-gastric, i.e., intra-abdominal pressure. Once the pressure within the balloon 21 reaches a stable reading of the intra-gastric pressure (i.e., a mean pressure level derived through an averaging process), the control device 20 can be configured to operate a pump 40 connected via filling line 22 to apply the esophageal seal pressure to the esophageal seal tamponade 53 via filling line 22. The esophageal seal pressure desirably can be regulated by the control device 20 on the basis of a predetermined $\Delta P$ value that can be preset in the software of the control device 20 and can be manually adjusted by a user via the input mechanism 26. The esophageal seal pressure calculates as the gastric pressure (measured by the gastric sensor 21) plus the $\Delta P$ value.

As schematically shown in FIG. 1, the filling fluid for the sensing balloon 21 and the esophageal seal tamponade 53 can be supplied from a fluid reservoir 35, which can hold a liquid or a gas, at room conditions or under pressure as the case may be.

Due to the particular membrane characteristics of the foil of the sealing esophageal bladder 53, a hydrostatic pressure gradient of about 10 cm to about 20 cm of water above the actual gastric pressure is considered desirable to produce a reliable seal against passive reflux of gastric contents. Typically, a hydrostatic $\Delta P$ pressure of up to about 10 cm is employed.

As schematically shown in FIG. 1, the actual esophageal seal pressure to be maintained in the esophageal seal bladder 53 can be constantly determined and adjusted by the control device 20 that operates a pump 40 connected via filling line 22. The control device 20 desirably is configured to derive this seal pressure from the actual intra-gastric pressure detected by the gastric balloon/electronic sensor 21 and the seal pressure gradient ΔP that has been set by the user via manual input mechanism 26. In order not to exceed a pressure level in the esophageal seal 53 that may cause tissue infarction and possibly cause ulcers, the control software employed by the control device 20 can be configured to contain a preset value $P_{esophagus\text{-}max}$, defining a maximum seal pressure not to be exceeded by the esophageal seal bladder 53.

The control device 20 desirably can be configured to permit the user to enter via input mechanism 27 a desired volume of feeding solution to be administered over a certain time period, whereby the duration of the delivery interval of the volume of the feeding solution to the patient can be separately defined or entered by the user via manual input mechanism 28 as another of a predefined set of parameters. The control device 20 can be configured to calculate a constant flow rate that is able to deliver the desired volume of feeding solution over the desired delivery period. The control device 20 desirably can be configured to operate the patient's nutrient feeding pump according to several modes, including the following examples.

—Operation Under Constant Flow:

This mode of operation calls for continuous adjustment of esophageal seal pressure according to a user defaulted seal pressure gradient, following operation of the feeding solution pump according to a machine calculated linear feeding rate, which is calculated to be able to deliver the desired volume of feeding solution over a desired time interval, automatically stopping of the feeding pump function when $P_{esophagus\text{-}max}$ is reached, pausing of the feeding pump function till $P_{esophagus}$ has dropped below $P_{esophagus\text{-}max}$, continuation of the feeding pump function according to the initially calculated feeding rate, till delivery of the desired total fluid volume of the feeding solution has been accomplished.

—Operation Under Dynamically Adjusting Flow—Delivery Volume Oriented:

This mode of operation calls for continuous adjustment of esophageal seal pressure to try to maintain a user-preselected defaulted seal pressure gradient A $P_{gastric}$. The control device 20 is configured to perform a continuous or intermittent determination of A $P_{gastric}$ over Δt (control software defined time intervals, e.g., 3 minutes before and after the actual pressure value determination), linear extrapolation of Δ $P_{gastric}$ over Δt, in case the slope of extrapolated pressure curve $P_{gastric}$ reaches $P_{esophagus\text{-}max}$ within Δt (or several Δt periods, or the total user determined delivery period), a reduction of the feeding solution flow rate is figured and executed by the control algorithm, which is configured to lower the slope of the extrapolation sufficiently so as not to exceed $P_{esophagus\text{-}max}$ within Δt (or several Δt periods, or the total user determined delivery period), dynamical extension of the feeding period till the desired total volume of feeding solution has been delivered.

—Operation Under Dynamically Adjusting Flow—Delivery Time Optimized:

This mode of operation calls for continuous adjustment of esophageal seal pressure according to a user-preselected defaulted seal pressure gradient, continuous or intermittent determination of Δ $P_{gastric}$ over Δt (control software defined time intervals, e.g. 3 minutes before and after the actual pressure value determination), linear extrapolation of slope (see above), if extrapolated pressure curve of $P_{gastric}$ does not reach $P_{esophagus\text{-}max}$ within Δt (or several Δt periods, or the total user determined delivery period), successive increase of flow rate to reach or nearly reach $P_{esophagus\text{-}max}$ within Δt (or several Δt periods, or the total user determined delivery period). Automatic stopping of the feeding pump function is effected when $P_{esophagus\text{-}max}$ is reached, the feeding pump function is paused till $P_{esophagus}$ has dropped below $P_{esophagus\text{-}max}$, the feeding pump function is resumed according to the prior calculated feeding rate of the feeding solution, till delivery of the desired total fluid volume of the feeding solution has been accomplished.

—Operation Under Dynamically Adjusting Flow—Delivery Time Optimized and Delivery Volume Oriented:

This mode of operation calls for operating according to the delivery time optimized mode as described above utill $P_{esophagus\text{-}max}$ is reached, then changing to the delivery volume oriented mode as described above.

Gravity-Operated Feeding Control:

The feeding solution can be supplied using gravity instead of by a mechanical pump. When the feeding process is gravity driven, the process can be controlled by an electronic occlusion element (not shown) that interrupts or gradually controls the flow and amount of the delivered feeding solution. A dripping chamber (not shown) can be integrated into a feeding line 19, and an optical detection device (not shown) can be used to detect and count the number of drops of feeding solution entering such chamber in order that the flow and volume of feeding solution can be detected and used to control the occlusion element. Thus, the above suggested control algorithms can be used in a manner similar to the computer program-assisted control described above.

ITP as a Parameter

By inflation of the esophageal bladder 53, the gastric probe 54 that can be introduced into the esophagus 15 is placed against the surface of the wall 16 of the esophagus 15, which in its middle portion and even better in its lower third transmits the pressure course inside the thorax through the wall 16 of the esophagus 15 (transmurally) to the esophageal placed bladder 53 of the gastric probe 54. The inter-transmural pressure (ITP) that is transmurally transmitted through the wall 16 of the esophagus 15 is detected by this bladder 53 and becomes a measured value that can be used as a control signal indicative of the pressure inside the esophagus 15 and that can enable the user to detect and monitor chest movement activity of the patient.

Probe Design Requirements:

The outer diameter of the delivery cannula 54 is advantageously between about 3 mm and about 6 mm, and especially between about 4 and about 5 mm. In the interior of the delivery cannula 54, in addition to a nutrient channel 61, through which liquid nutrients are delivered to the patient, there is a delivery channel 62, via which the inflatable bladder 53 can be filled with a fluid, whether gaseous or liquid.

The performance of the device and the method, to prevent gastric content from ascending into a patient's pharynx via the esophagus 15, further depends on the specific design and a particular performance of the esophageal sealing bladder 53. To prevent pressure-induced esophageal lesions, the present invention describes a low-pressure bladder tamponade/occlusion of the esophageal organ lumen. Next to the prevention of pressure induced esophageal lesions, the esophageal sealing bladder 53 must be configured to meet the requirements of permanent placement inside the esophagus' highly dynamic structure that is constantly in movement and changing cross-sectional mucosal folding and shape. On account of these difficulties, the search for a simple designed intra-esophageal bladder seal, which is atraumatic, not irritating, withstanding peristaltic movement, and effecting a sufficient mechanical separation of airway and digestive tract, could not until now be satisfactorily resolved. The functional features of the invented bladder equipped decompression probe described in the invention meet such requirements.

Residual Bladder

Figures 2, 3:
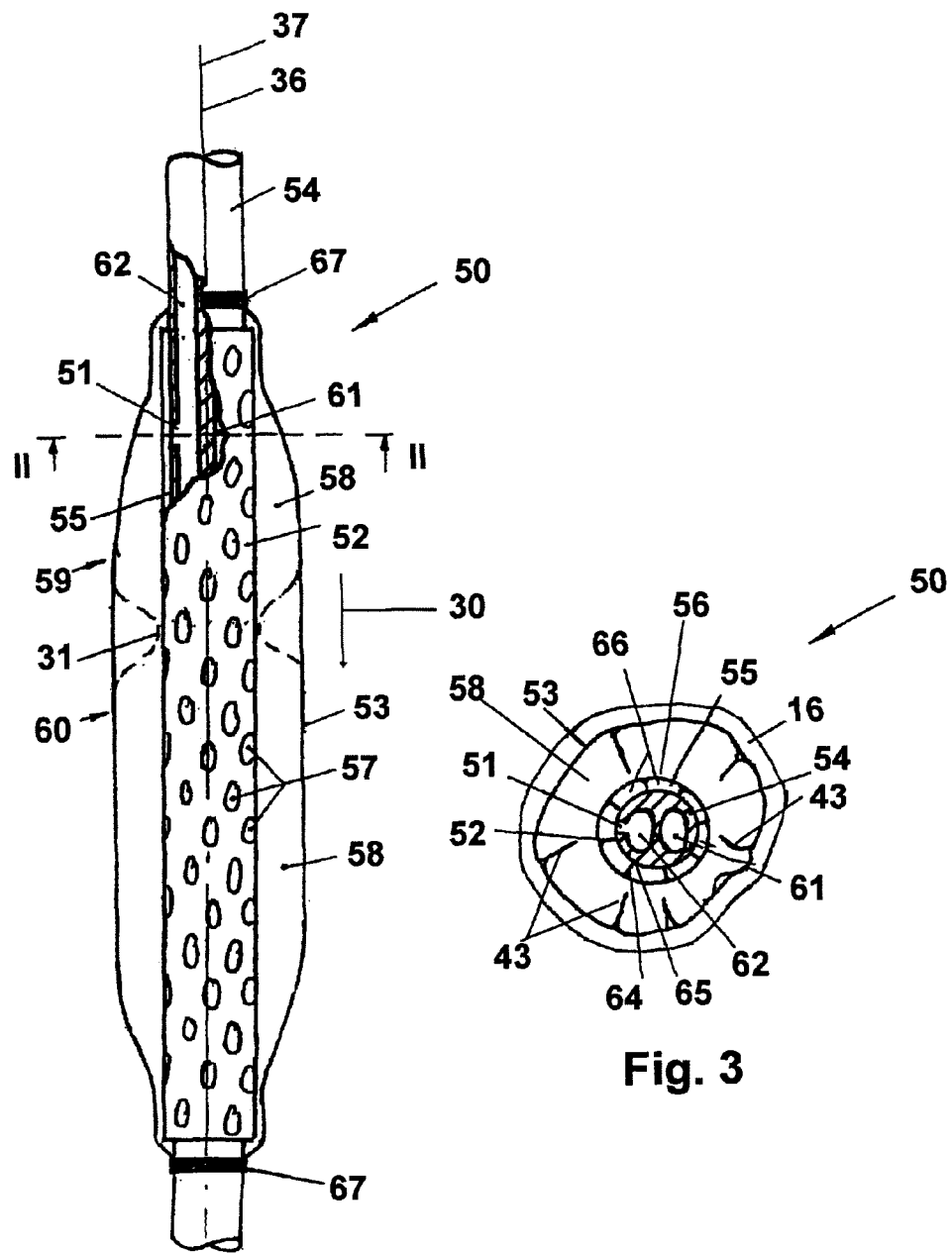
FIG. 2 is partial cut-away illustration of an embodiment of the esophageal bladder device and feeding tube according to an embodiment of the present invention.
FIG. 3 is a cross-sectional view of the device shown in FIG. 2, along line II-II, as it may sit in the esophagus.

The diameter of the inflatable bladder 53 in a freely unfolded condition is between about 20 mm and about 50 mm. A diameter of about 30 mm to about 40 mm is particularly desirable for the diameter of the inflatable bladder 53 in a freely unfolded condition. The tampooning bladder 53, when freely inflated to its full pre-shaped dimension, has a larger diameter than that of the expected distended esophagus 15. Hence, as schematically shown in FIG. 3, the sealing bladder 53 includes a residual volume 58 that is able to engage with the ridges and pleated lining of the esophagus without separating from contact with the pre-shaped, undistended dimensions of the esophageal wall 16. As schematically shown in FIG. 3, the residual diameter of the tampon bladder 53 further creates a number of reserve interpleatings 43 along its surface in order to ensure that the pleated lumen of the esophagus can be securely covered by the bladder hull over its entire circumference without having to distend or stretch the bladder material in order to effect an organ lumen obstruction. Due to the prevention of any stretch of the bladder hull, the pressures inside the bladder 53 needed to effect the desired sealing therefore can be kept low, in the ideal case only slightly exceeding intra-luminal organ pressure by a few millibars (cm $H_2O$), enabling a fluid seal at filling pressures that can be kept below perfusion relevant trans-mural forces, and enabling the user to set the barometrically measured pressure inside the bladder 53 equal to such effected trans-mural forces.

Bladder Thickness

In order to meet the various design requirements on an atraumatic sealing intra-esophageal bladder 53 in the best possible way, the bladder 53 ideally is preferably made from microthin-walled, easily pliable plastic film with a wall thickness of less than or equal to about 0.03 mm. The seal bladder 53 is subjected to a fill pressure of less than or equal to 30 mbar, being set ideally within a pressure range of about 10 mbar to about 20 mbar, which are pressures that are known to be non-critical for tissue perfusion, and granting a sufficient degree of compatibility to the motility of the esophagus 15. The bladder 53 can be made of blow-moulded, foil-welded, or dipped material. The bladder 53 can be made from polyurethanes, polyethylenes, silicone, natural and synthetic rubbers, polyvinylchloride, or other materials offering adequate pliability and stability in the required foil thickness range.

Bladder Length:

The membrane forming the esophageal bladder 53 is ideally sized to cover the entire length of the esophagus. The bladder body preferably is sized so that it can extend between the upper and the lower esophageal sphincter. In most embodiments, the tampon-bladder 53 usually has a length of about 6 cm to about 15 cm, desirably about 6 cm to about 9 cm.

Adjacent Organs

Further, the invention considers immediately adjoining structures such as the great vessels, the accompanying nerves, the trachea and main bronchi, the lungs 12 themselves and, not least, the heart, particularly the left atrium. In contrast to conventional blocking techniques, the invented reflux-sealing esophageal probe does not endanger such structures due to perfusion or tissue critical pressures effected by the permanent pressurized bladder seal element 53.

Filling Media

Different fluids may be used as the medium for filling the esophageal seal bladder 53, depending on the application. A presently preferred bladder filling medium, which is distinguished by compressibility as well as a certain adaptability of its own to the fluctuations mentioned below is, for instance, a gaseous one. Air is a presently preferred gas to provide the fluid medium for filling the esophageal sealing bladder 53, and gas mixtures can be used. However, a liquid medium for filling of the esophageal seal bladder 53 is possible and viscous liquids, water, or gas/liquid mixtures such as air and water, can be used.

Shift of the Bladder Filling Medium During Peristaltic, Lengthwise Directed Contraction of the Esophagus (Swallowing):

Desirably, the invented probe 50 can be equipped with a special mechanism, which permits an intra-bladder shift of the bladder filling medium within the esophageal sealing bladder 53, giving the device the required ability to remain stationary in the location where it is placed and preventing a transport of the bladder equipped probe 50 towards the stomach and/or preventing patient irritating pressure peaks (bolus sensations) being generated in the esophagus by the filling medium accumulating in the lower portion of the seal bladder 53, below the peristaltic contraction wave. As schematically shown in FIG. 3, within the segment of the probe 50 that carries the bladder 53, the device can include a second lumen 62 that is disposed next to the drainage or decompression lumen 61. As schematically shown in FIG. 2, the drainage lumen 61 can be arranged relative to the second lumen 62 in a manner such that a channel 55 is formed between the interior 58 of the bladder 53 and the second lumen 62. The second lumen 62 can be positioned relative to the interior 58 of the bladder 53 by means of dividing fixtures or baffle-like structures that bridge the passageway defining the channel 55.

As schematically shown in FIG. 2, a conduit 52 that is disposed around the feeding tube 54 can be configured to channel the air or other gaseous medium filling the esophageal bladder 53 so as to be redistributed with each wave of a peristaltic contraction from the bladder portion 60 that is disposed below the peristaltic wave into the bladder portion 59 that is disposed above and already released from the peristaltic wave. In this way, an intra-bladder shift of the filling medium is effected to accommodate the peristaltic wave imposed on the esophagus. As shown in accompanying FIGS. 4-7 for example, the described particular tube shaft profile within the bladder carrying tube segment facilitates the volume shift that prevents undesired pressure increases in the tamponade 53, pressure increases that otherwise could pose a painful irritation of the patient.

The inner cavity 58 of the tampon-bladder 53 may be filled with a medium, through a delivery channel 55 lying between the delivery lumen 62 and the inner cavity 58 of the tampon-bladder 53, from a filling line 22 connected to the channel 55 via the delivery lumen 62. As schematically shown in FIG. 1, simply operated examples of such a filling device are a reservoir or equalizing vessel 35, particularly one situated outside the patient and connected via filling line 22. A supply of the filling medium sufficient to fill the inner cavity of the tampon-bladder 53, and in addition to allow for the above-mentioned functional fluctuations of the lumen and the tonus of the esophageal wall 16 through further outflow or intake of the medium by expansion and collapse of the tampon-bladder 53, is kept in the reservoir or equalizing vessel 35.

In this connection it could be seen as an additional advantage for the bladder filling medium to be actively led into the inner cavity 58 of the tampon-bladder 53 or withdrawn from the inner cavity through the channel 55. Such active supply and withdrawal desirably can take place through a pump 40 that is operated by the control device and that is regulated preferably to compensate for any extensive pressure-passive fluctuations in the tampon-bladder 53.

Stomach Probe, Volume Shift Mechanism, Advanced Profiles:

FIG. 2 illustrates the basic construction of an embodiment of an anti-gastric reflux esophageal-stomach probe 50 according to the present invention. A shaped, conduit body 52 is superimposed around and over a delivery cannula 54 in the region of an inflatable bladder 53. The conduit body 52 encloses a lumen 55 in its interior. The lumen 55 also is shown in the view of FIG. 3, which represents the cross section II-II through the stomach probe shown in FIG. 2. In this example of the embodiment, the lumen 55 is located between the delivery cannula 54 and the surface 56 of the conduit body 52.

As can be seen in FIG. 2, several openings 57 defined through the surface 56 of the shaped body 52 and desirably are distributed over the entire surface 56 of the shaped body 52. The lumen 55 is connected to the interior 58 of the inflatable bladder 53 via the openings 57. This means that the openings 57 are configured and disposed to permit volume or fluid exchange between the lumen 55 and the interior 58 of the inflatable bladder 53.

FIG. 4 shows an enlarged image of the disclosed shaped body 52 as shown in the first embodiment of the invention shown in FIG. 2 wherein the shaped body 52 has an almost cylindrical external shape. The number and shape of the openings 57 defined through the surface 56 of the shaped body 52 may vary, depending on the end use. In addition to the approximately round or oval openings 57 shown in FIGS. 2 and 4 for example, the openings 57 may also be elongated, for example. The shape or contour of the openings 57 may vary from being a largely round or oval cross-sectional profile, to triangular, quadrangular or polygonal shaped openings 57. Nor must the openings 57 be distributed more or less evenly over the surface 56 of the conduit body 52 as in the embodiment shown in FIGS. 2 and 4. Alternatively, the openings 57 may also be distributed unevenly. In this case, it is important that the shape and arrangement of the openings 57 permit adequate volume exchange between two sections, 59 and 60, of the inflatable bladder 53. The number of openings 57 may vary from one to any number of individual openings, e.g. 100 or 1000 openings. The number of openings 57 is restricted only by the area of the surface 56 of the conduit body 52 and the shape of the openings 57.

In one embodiment of the invention, the cross section of the shaped body 52 may have several wall sections 64. As shown in FIG. 4 for example, several wall sections 64 extend radially from the cylindrical surface 56 of the shaped body 52 into the interior of the shaped body 52. The free, front ends 65 of the wall sections 64 define a diameter, which corresponds approximately to the outer diameter of the delivery cannula 54 and which are supported at the delivery cannula 54 of the probe 50 and, together with it, define at least one section 66 of the lumen 55. As shown in FIG. 3 for example, when the shaped body 52 is located on the delivery cannula 54, the front ends 65 of the wall sections 64 rest on the delivery cannula 54. The wall sections 64 may extend in a roughly star-shaped configuration into the interior of the shaped body 52. This arrangement guarantees an approximately even distribution of the wall sections 64 and in turn guarantees secure support and retention of the shaped body 52.

As shown in FIG. 3, together with the delivery cannula 54, the lumen 55 inside the shaped body 52 can be divided into separate lumen sections 66. A single lumen section 66 is delimited by two wall sections 64, the portion of the surface of the shaped body 56 which lies between the two wall sections 13 and the portion of the surface of the delivery cannula 54 which is located between the contact surfaces of the front ends 65 of the wall sections 64. In this example of the embodiment shown in FIGS. 2, 3 and 4, the shaped body 52 has eight wall sections 64, which all extend in a finger-like manner by roughly the same amount into the shaped body 52. These wall sections 64 can form a passageway with their front ends 65, whose dimensions correspond approximately to those of the delivery cannula 54. The shaped body 52 can therefore be mounted easily onto the delivery cannula 54.

In other embodiments of the invention, the number of wall sections 64, however, may vary arbitrarily, and thus influence the shape of the lumen 55 or the individual lumen sections 66. The depth to which the wall sections 64 penetrate into the interior of the shaped body 52 also may vary, and this depth determines the position of the shaped body 52 in relation to the delivery cannula 54. Depending on the particular application, the longitudinal axis 36 of the shaped body 52 may also be displaced in relation to the longitudinal axis 37 of the delivery cannula 54. This means that the shaped body 52 need not necessarily sit more or less concentrically on the delivery cannula 54 as in the embodiment shown in FIGS. 2, 3 and 4 where the longitudinal axis 36 of the shaped body 52 coincides with the longitudinal axis 37 of the delivery cannula 54.

In the region of the axial front side of the shaped body 52, the lumen 55 may expediently be connected to a delivery channel 62, via which the inflatable bladder 53 can be filled with a fluid. In this embodiment shown in FIGS. 2 and 3, the delivery channel 62 for the filling fluid extends, at least in parts, into the conduit body 52 and has at least one access opening 51, which connects the delivery channel 62 to the lumen 55 and joins the lumen 55 with the interior 58 of the inflatable bladder 53. The access opening 51 guarantees good volume equalization between the sections of the inflatable bladder 53, and can also be produced using simple techniques. The access opening 51 may extend over roughly the entire length of the shaped body 52. As schematically shown in FIGS. 2 and 3 for example, the shaped body 52 may have at least one access opening 51 which extends in roughly the longitudinal direction of the shaped body 52 over at least 50 to 60%, preferably over up to 70%, and especially over up to 80%, of the total length of the shaped body. This arrangement can be produced using simple techniques and simplifies the construction of the stomach probe 50, since the inflatable bladder 53 can be filled directly via the lumen 55 with which it is connected.

In embodiment shown in FIGS. 2 and 3, the access opening 51 runs radially in relation to the shaped body 52. The access opening 51 of the delivery channel 62 need not necessarily run radially, but may also run in the region around the axial front surface of the shaped body 52 rather than axially to the shaped body 52. In other embodiments of the disclosed stomach probe 50, the delivery channel 62 also may run along the outside of the delivery cannula 54. As shown in FIG. 5, the delivery channel 62 may, for example, be located, at least partly, in an indentation 63, which runs along the delivery cannula 54.

FIGS. 6 through 10 show perspective views of further embodiments of the disclosed shaped body 52. FIGS. 6 and 7 show second and third embodiments of the disclosed shaped body 52. The reference numbers used in FIGS. 2 through 5 refer to the same components as those in FIGS. 6 and 7.

As shown in FIGS. 6 and 7, each shaped body 52 can have a central, roughly tubular structure 68, with a roughly circular transverse cross section. The inner diameter of the shaped body 52, as well as the contact surface between the shaped body 52 and the delivery cannula 54, are formed by the tubular structure 68. As shown in FIG. 7, the shape of the inner cover surface 69 roughly corresponds to the shape of the surface of the delivery cannula 54. As shown in FIGS. 6 and 7, several wall sections 70 extend radially outwards from the central, tubular structure 68. At the outermost end 71 of each wall section 70 lying opposite to the central, tubular structure 68 is a surface 72, which runs roughly transversely to the wall section 70.

In the embodiment of FIG. 6, the shaped body 52 has four wall sections 70 arranged roughly in a circle. The wall sections 70, together with the associated surfaces 72, form an approximately T-shaped profile in the cross section. This T-shaped profile can be produced easily, and provides a lumen 55 of sufficient size, as well as a good contact surface for the inflatable bladder 53. In the embodiment of FIG. 7, the shaped body 52 has five wall sections 70 arranged in an approximate star-shaped configuration around the tubular structure 68. In the embodiment of FIG. 7, the wall sections 70, together with their respective transverse surfaces 72, form a roughly L-shaped profile in cross section. This L-shaped profile can also be produced using simple techniques, and provides for a lumen and contact surface that permits rapid volume exchange between the sections of the inflatable bladder 53.

The T- and L-shaped profiles of the shaped bodies 52 shown in FIGS. 6 and 7 are located at such a distance from each other, or are dimensioned in such a way, that the transverse surfaces 72 of two adjacent T- or L-shaped profiles are at a distance from each other. This means that every two of the transverse surfaces 72, which define the surface 56 of the shaped body 52, define an opening 73 or slit, which runs along the length of the shaped body 52. In these examples of the embodiment shown in FIGS. 6 and 7, the lumen 55, which is located here between the transverse surfaces 72 and the tubular structure 68, is divided by the T-shaped profiles or L-shaped profiles into separate lumen sections 66. The shape of an individual lumen section 66 is thereby determined by in each case two adjacent T-shaped profiles or L-shaped profiles and the portion of the surface 56 of the tubular structure 68 enclosed by them. The number of wall sections 70 may be varied, depending on the end use. If this end use changes, the shape and the number of lumen sections 66 and openings 73 in the surface 56 of the shaped body 52 also desirably change.

In a further embodiment of the invention, the wall sections 70 may also be arranged unevenly around the tubular structure 68, unlike the examples shown here. The transverse surfaces 72 at the ends 71 of the wall sections 70 also can be dispensed with in some embodiments. In this case, the surface 56 of the shaped body 52 is determined by the ends 71 of the wall sections 70. The number of wall sections 70 may be increased accordingly, and there may be between about 5 and about 15 wall sections 70, for example.

The abovementioned first through fourth embodiments of the disclosed shaped body 52 in FIGS. 2-7 also can be twisted, rather like a screw, and thus can be shaped like a coil.

Figure 8:
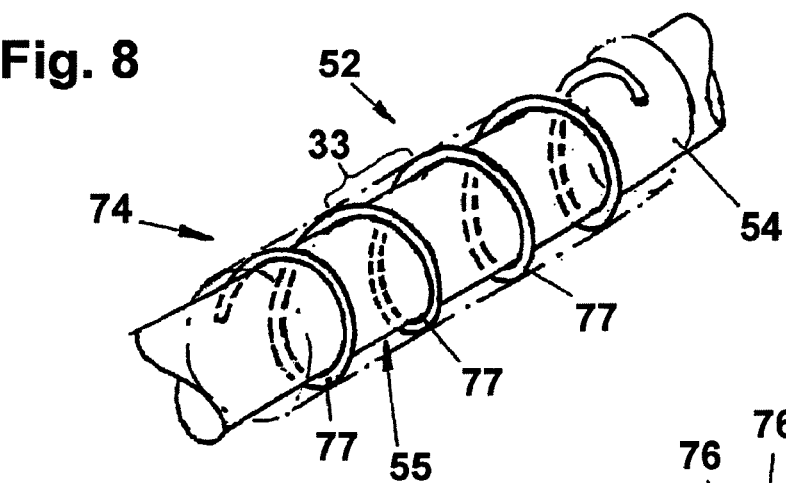
FIG. 8 shows a schematic view of an alternative design for the ferrule.

FIG. 8 shows a further embodiment of the disclosed shaped body 52 in the form of a spiral that is formed as a coil 74. The inner diameter of the coil 74 corresponds approximately to the outer diameter of the delivery cannula 54. In this embodiment, the lumen 55 also has a spiral shape. In use, that is when the shaped body 52 is located on the delivery cannula 54, as shown in FIG. 8, the coil 74 is defined by a plurality of consecutive windings 77. Each winding 77 of the coil 74 helically wraps once completely around the delivery cannula 54. As shown in FIG. 8, an opening 33, which runs spirally around the delivery cannula 54, is defined between the individual windings 77 of the coil 74 and encloses the lumen 55. The thickness of the coil 74 determines the height of the lumen 55. The coil 74 may have a roughly circular cross section. However, alternatively, the cross section of the coil 74 may have an oval shape or angular shape.

With the coil 74 of the shaped body 52 shown in FIG. 8, the inner diameter of the shaped body 52 is determined by the inner diameter of the coil 74. The contact surface between the shaped body 52 and the delivery cannula 54 corresponds, in this case, to the spiral installation line or surface of the individual windings 77 of the coil 74. Whether it is in the form of a line or a planar configuration will be determined by the cross section of the coil 74.

In addition to single or interconnected coils, a pipe-like or tubular structure also can be applied. As shown in FIG. 8 by a line consisting of a sequence of dots and dashes, pipe-like or tubular structure can have openings. The external shape of this type of shaped body 52 would then be similar to the shaped body shown in FIG. 2.

In a further embodiment, the lumen 55 may also be defined by several coils, for example two coils, which are roughly concentrically disposed so that the one is on top of, i.e., surrounding, the other. In this case, the two coils may have the same gradient or different gradients. The coils also can be superimposed so that each one runs in opposite direction to the other one. In this case, the lumen 55 is defined by the intermediate space between the individual windings of the relevant coil, i.e., by the overlapped sections of these intermediate spaces.

Figure 9:
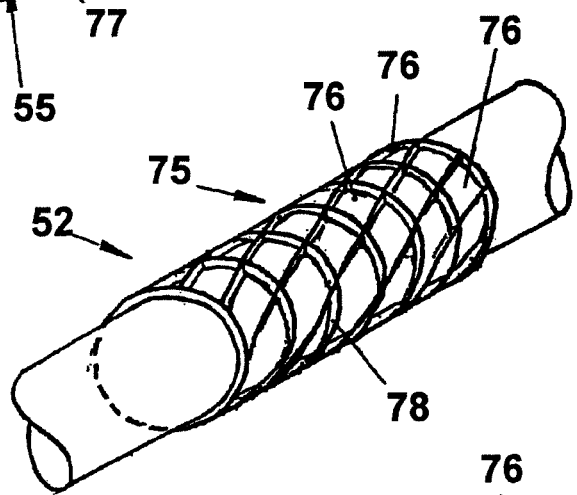
FIGS. 9 and 10 show variations of the design of FIG. 8.

FIG. 9 shows another embodiment of the disclosed shaped body 52 that is pipe-like or tubular in shape and has a net-like construction 25. The inner diameter of the shaped body 52 corresponds approximately to the outer diameter of the delivery cannula 54. As shown in FIG. 9, the net-like construction 75, the inner diameter of the shaped body 52 and the contact surface between the shaped body 52 and the delivery cannula 54 are determined by the individual connecting pieces 78 of the net-like construction 75. In this embodiment shown in FIG. 9, the lumen 55 is located within the mesh or openings 76 of the net-like construction 75, which are at least partly connected to each other, and thus permit volume exchange between the individual openings 76 of the net-like construction 75.

Figure 10:
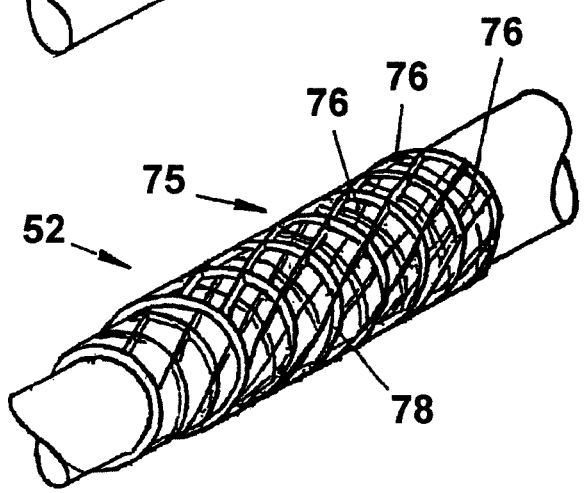

In a further embodiment of the invention, the shaped body 52 may also comprise several layers of the net-like construction 75, as FIG. 10 shows. These layers of the net-like construction 75 are arranged roughly concentrically in relation to each other, whereby the inner diameter of the innermost layer corresponds approximately to the outer diameter of the delivery cannula 54. In this embodiment, the lumen 55 is defined by the holes 76 in the net-like construction 75, which overlap at least in parts. This means that the overlapping holes 76 of the individual layers of the net-like construction 75 form channels or individual lumen sections 66. When the shaped body 52 is in the state it is in during use, i.e., when the shaped body 52 is located on the delivery cannula 54, at least part of the lumen section 66 extends at least in sections along the delivery cannula 54, and thus permits volume exchange between the individual sections of the inflatable bladder 53. This net-like construction can be produced efficiently and can be premounted onto the coil, and so can simplify assembly.

The dimensions of the different embodiments of the shaped body 52 described here may vary, depending on the end use. In practice, however, an approximate length of about 6 cm to about 12 cm, and especially a length of about 6 cm to about 9 cm, has proved to be particularly advantageous for the shaped body 52. They provide a sufficiently large contact surface for the inflatable bladder 53. At the same time, an adequate volume exchange between all the sections of the inflatable bladder 53 is guaranteed. The outer diameter of the shaped body 52 also depends on the end use, as well as on the dimensions of the delivery cannula 54 and the inflatable bladder 53, and is advantageously in the region of between about 7 mm and about 12 mm, and especially between about 6 mm and about 8 mm. These dimensions guarantee good volume exchange between the sections of the inflatable bladder 53. However, for special end uses, the dimensions of the shaped body 52 may deviate from the abovementioned dimensions.

The inflatable bladder 53 is filled with a fluid, e.g., water, via the delivery channel 62, whereby the fluid flows through the access opening 51 of the delivery channel 62 into the lumen 55 of the shaped body 52. The fluid flows into the interior 58 of the inflatable bladder 53 through the openings 57, 73, 76 and 33 of the shaped body 52. As the inflatable bladder 53 fills with the fluid, the inflatable bladder 53 expands until at least a portion of its exterior surface lies almost completely against an uninterrupted annular portion of the wall 16 of the esophagus 15, as can be seen in FIG. 3. This enables the esophagus to largely be sealed off from liquids or solid substances, which tend to move up from the region of the stomach 18 towards the pharyngeal cavity, and thus to keep the windpipe free from harmful substances.

The swallowing motions made by the patient who has been fitted with the disclosed stomach probe 50 cause the muscles to contract along the wall 16 of the esophagus 15. These muscles create one or usually several annular constrictions in the esophagus 15, which are propagated along the esophagus 15 from the larynx region towards the stomach 18.

In order to illustrate the functions of the shaped body 52, the movement of a single, annular constriction will now be examined. In the area around the inflatable bladder 53, the annular constriction in the esophagus causes a partial reduction in the outer diameter of the inflatable bladder 53, i.e., a local narrowing 31 of the inflatable bladder 53 occurs, which is shown in FIG. 2 as a dashed line. This narrowing 31 divides the inflatable bladder 53 into two sections, 59 and 60. While the esophageal constriction is imposed as a wave that moves along the inflatable bladder 53 as when swallowing occurs, the dimensions of the individual sections, 59 and 60, change. In this case employing the probe 50 of the present invention, however, the volume of fluid that can be contained in the relevant sections, 59 and 60, of the inflatable bladder 53, also changes. The disclosed shaped body 52 provides a lumen 55, which permits rapid volume exchange between the individual sections, 59 and 60, of the inflatable bladder 53. The surface 56 of the disclosed shaped body 52 provides, if necessary, a relatively rigid contact surface for the constricted wall section 31 of the inflatable bladder 53. The lumen 55 is therefore kept free of these external influences, and is available entirely for volume exchange. As schematically shown in FIG. 2, while the constriction 31 moves along the inflatable bladder 53 in the direction of arrow 30, the fluid is forced out of the interior 58 of the second section 60 of the inflatable bladder 53 via the openings 57 beneath the second section 60 of the inflatable bladder 53, and the fluid is forced into the interior 58 of the first section 59 of the inflatable bladder 53 via the openings 57 beneath the first section 59 of the inflatable bladder 53.

A stomach probe of the type disclosed in German Utility Model Application No. 202006002832.3 has been improved in the present disclosure. In accordance with the present invention, the lumen 55, which is located between the delivery cannula 54 and the inflatable esophageal seal 53 and which is connected to the interior 58 of the inflatable esophageal seal 53, can be produced by a relatively simple technique, and at the same time guarantees adequate volume equalization between the partial volumes of the inflatable esophageal seal 53.

The separate shaped body 52 of the stomach probe 50 can be produced by a simple technique, since it can be prefabricated as a separate component. The shaped body 52 described above is preferably made from plastic and is produced desirably by an extrusion process. This manufacturing process enables the shaped body 52 to be produced by a relatively simple and quick technique. Alternatively, the shaped body 52 may be produced by casting or injection molding.

In principle, the materials used for the shaped body 52 are ones that can deform easily to suit the human body, i.e., they do not injure the patient whilst being inserted or during long-term use of the probe, but they are rigid enough to provide a non-collapsible shape when peristalsis occurs over the shaped body 52. Advantageous materials are, for example, PVC, PUR, blends of PVC and PUR, blends of PUR and polyamides, and/or silicones. These materials guarantee good compatibility with the tissue of the patient. These materials can be shaped easily and thus reduce the risk of injury during introduction of the stomach probe 50 into the patient, yet these materials are stable enough to maintain the lumen 55 during peristalsis.

During assembly of the stomach probe 50, the separate shaped body 52 desirably can be mounted as a finished component on the delivery cannula 54, and attached to the delivery cannula 54. Applying the shaped body 52 to the delivery cannula 54 determines the shape of the lumen 55 at the same time, which ensures that there is sufficiently rapid volume exchange between the sections of the inflatable esophageal seal 53. This configuration simplifies assembly of the stomach probe 50, since the number of individual processing stages needed to produce the lumen 55 can be reduced. Such simplified assembly results in a potential for reducing both time and costs when producing the stomach probe 50.

The shaped body 52 may have a tubular structure, whose internal shape corresponds roughly to the external shape of the delivery cannula 54. The tubular structure enables the shaped body 52 to be attached roughly concentrically to the delivery cannula 54. These complementary shapes simplify the assembly process for the disclosed stomach probe 50, as the shaped body 52 desirably can be applied to the delivery cannula 54 by means of a sliding process. Since the inner diameter of the relevant shaped body 52 corresponds approximately to the outer diameter of the delivery cannula 54, or is at least slightly smaller than the outer diameter of the delivery cannula 54, a slight press-fitting effect occurs during mounting of the shaped body 52 onto the delivery cannula 54. The resulting static friction fixes the shaped body 52 radially and axially onto the delivery cannula 54 and guarantees axial and/or radial fixing of the shaped body 52 on the delivery cannula 54 of the stomach probe 50.

Alternatively, the shaped body 52 may also be fixed onto the delivery cannula 54 by means of adhesion, e.g., by applying an adhesive at least on part of the contact surface between the shaped body 52 and the delivery cannula 54. Alternatively, the shaped body 52 may also be fixed by material-bonding whereby, for example, at least part of the contact surface between the shaped body 52 and the delivery cannula 54 is treated with a solvent. Solvent etching of the shaped body 52, and/or the delivery cannula 54, at least in part, guarantees good bonding of the two components. In principle, any possible combination of the above-mentioned fixing techniques are feasible as a means of attaching the shaped body 52 onto the delivery cannula 54.

The final, assembled stomach probe 50 desirably can be used for treating comatose patients, for example, who are unable to feed themselves. In this application, the disclosed stomach probe 50, i.e., the delivery cannula 54 of the stomach probe 50, is inserted into the patient's esophagus, whereby the section of the stomach probe 50 that is fitted with the inflatable bladder 53 is located above the entrance to the stomach 18 in the esophagus 15. The presently preferred length of the shaped body 52 of approximately about 6 cm to about 9 cm ensures that the shaped body 52 fits well in the section between the upper and lower sphincter of the esophagus.

To improve orientation, the stomach probe 50 may be fitted with at least one radiopaque marker, such as a metal ring 67. The radiopaque marker 67 makes it possible to check that the probe 50 is in the correct position by means of an X-ray image. The marker 67 facilitates positioning of the probe 50 in the patient and acts as a reference point to orientating organs, such as the diaphragm and/or thyroid, on the X-ray image of the thorax. As shown in FIG. 2, more than one marker 67 may be employed. These radiopaque markers 67 may be placed at the shaped body 52, the delivery cannula 54 and/or the inflatable bladder 53.

I claim:

1. An anti-gastro-esophageal reflux device for use during enteral feeding, the device comprising:
    a pressure-regulating unit;
    a tube having a double lumen, a gastric balloon, and an esophageal bladder, said gastric balloon being connected by a first conduit to said pressure-regulating unit and configured to be disposed in the patient's stomach to sense the gastric pressure therein, said esophageal bladder being connected by a second conduit to said pressure-regulating unit, said esophageal bladder having a compressible volume and an outer surface with a plurality of pleats that are configured to intermesh with a patient's esophagus wall structures, and said pressure-regulating unit being configured to maintain a pressure within said esophageal bladder at a level greater than the gastric pressure exerted on said gastric balloon when the anti-gastro-esophageal reflux device is in use.

2. An anti-gastro-esophageal reflux device for use during enteral feeding, the device comprising:
    a tube having a double lumen;
    a gastric pressure sensor configured to be disposed in the patient's stomach to sense the gastric pressure therein and configured for monitoring gastric pressure when enteral feeding is in process;
    an esophageal bladder having a compressible volume and an outer surface with a plurality of pleats that are configured to intermesh with a patient's esophagus wall structures;
    a control device that is connected via a first conduit to said esophageal bladder and configured to regulate fluid pressure within said esophageal bladder, said gastric pressure sensor being connected in communication with said control device, said control device including a filter algorithm configured to provide an averaged signal from signals received from said gastric pressure sensor, said control device being configured to add a pre-set gradient value to said averaged signal to define a relative level of esophageal seal pressure, and said control device being configured to maintain said relative level of esophageal seal pressure within said esophageal bladder when the anti-gastro-esophageal reflux device is in use.

3. An anti-gastro-esophageal reflux device according to claim 2, further comprising:
    a feeding pump configured to deliver feeding solution at a feeding rate over a time interval, said feeding pump being configured to sense the relative amount of pressure in a patient's stomach as well as the relative amount of pressure in a patient's esophagus and to adjust the feeding rate according to the relative amount of pressure in a patient's stomach as well as the relative amount of pressure in a patient's esophagus when the anti-gastro-esophageal reflux device is in use.

4. An enteral-feeding device comprising: an automatable feeding pump; a control device having a feedback sensor for sensing a pressure gradient between the pressure in a patient's stomach and the pressure in a patient's esophagus, said control device being configured for controlling and monitoring the pump's feeding rate to the patient as a function of said pressure gradient; a pressure-regulating unit; a tube having a double lumen, a gastric balloon, and an esophageal bladder, said gastric balloon being connected by a first conduit to said pressure-regulating unit and configured to be disposed in the patient's stomach to sense the gastric pressure therein, said esophageal bladder being connected by a second conduit to said pressure-regulating unit, said esophageal bladder having a compressible volume and an outer surface with a plurality of pleats that are configured to intermesh with a patient's esophagus wall structures, and said pressure-regulating unit being configured to maintain a pressure within said esophageal bladder at a level greater than the gastric pressure exerted on said gastric balloon when the anti-gastro-esophageal reflux device is in use.

5. An enteral-feeding device according to claim 4, wherein said feedback sensor includes a gastric balloon and an esophageal bladder.

6. An enteral-feeding device according to claim 4, wherein said control device includes a timer device configured for controlling said feeding rate, and wherein said timer device can be adjusted either manually or electronically as a function of said pressure gradient and the amount of feeding solution to be fed to the patient.

7. An enteral-feeding device according to claim 5, wherein said control device is configured to deliver a defined volume of fluid into said gastric balloon to fill said balloon to a volume smaller than the gastric balloon itself in its freely inflated preshaped state.

8. An enteral-feeding device according to claim 7, wherein said gastric balloon is inflated up to about 75-80% of a volume in free inflation without hull distension.

9. An enteral-feeding device according to claim 4, wherein once a pressure in said gastric balloon reaches a stable reading of the intra-gastric filling pressure, said control device is configured to regulate said esophageal seal pressure at a predetermined value that is calculated by computer software or that is defined by a user.

10. An enteral-feeding device according to claim 4, wherein a desired value for a range or limit for the pressure gradient ($\Delta P$), affecting esophageal pressure parameters, is calculated thus: the pressure in the patient's stomach+$\Delta P$ value.

11. An enteral-feeding device according to claim 4, wherein said feedback sensor is a gastric balloon and said control device is configured to adjust the pressure in said gastric balloon to compensate for changes in pressure and conditions in the patient's abdominal and thoracic cavities contiguously over a course of enteral feeding.

12. An enteral-feeding device according to claim 4, wherein said control device is configured to permit a user to enter a desired feeding volume to be administered over a predetermined period, such that volume and time values can be separately defined and programmed to achieve the desired feeding regime.

13. An enteral feeding device according to claim 4, wherein said control device includes computer software that determines an actual rate of feed volume delivered over a primary feeding time interval.

14. An enteral-feeding device according to claim 4, wherein said control device has a visual display for volume/time calculations and is programmable by a user to enter a desired feeding time interval and calculate a volume of feeding solution delivered within a preset unit of time or over an entire contiguous feeding period selected.

15. An enteral feeding device according to claim 4, wherein said control device has a memory system that enables said control device to apply a software-preset or user-defined feeding rate to determine relative compliance of a patient's stomach against said feed volume.

16. An enteral feeding device according to claim 4, wherein said control device automatically increases a slope of a determined graph (V/P), based on relative pressure increase over an applied volume, to reach a desired volume ($V/t_{total}$).

17. An enteral-feeding device according to claim 4, wherein once said feedback sensor detects a maximum gastric under a given parameter setting, said control device will pause said feeding pump intra-gastric pressure has sufficiently decreased to within predetermined feeding levels before controlling said pump to resume feeding the patient.

18. An enteral-feeding device according to claim 4, wherein said control device is configured to calculate and determine continuously, hourly and expected feeding volumes over a selected time interval.

* * * * *